(12) United States Patent
Koike et al.

(10) Patent No.: US 6,521,774 B2
(45) Date of Patent: Feb. 18, 2003

(54) ORGANOSILICON COMPOUNDS

(75) Inventors: Noriyuki Koike, Gunma-ken (JP); Koichi Yamaguchi, Gunma-ken (JP); Yasunori Sakano, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/841,047

(22) Filed: Apr. 25, 2001

(65) Prior Publication Data

US 2001/0044495 A1 Nov. 22, 2001

(30) Foreign Application Priority Data

Apr. 25, 2000 (JP) ......................................... 2000-124108

(51) Int. Cl.$^7$ .................................................. C07F 7/04
(52) U.S. Cl. ........................ 556/435; 556/431; 528/31; 528/35
(58) Field of Search ................................. 556/435, 431; 528/31, 35

(56) References Cited

U.S. PATENT DOCUMENTS

| 2,507,514 A | * | 5/1950 | Clark | 556/435 |
| 3,328,448 A | * | 6/1967 | Barnes et al. | 260/448.2 |
| 3,496,206 A | * | 2/1970 | Berger | 260/448.2 |
| 5,260,468 A | * | 11/1993 | Yamamoto et al. | 556/431 |
| 5,391,794 A | * | 2/1995 | Jung et al. | 549/215 |
| 5,399,740 A | * | 3/1995 | Jung et al. | 556/435 |
| 5,453,528 A | * | 9/1995 | Boutevin et al. | 556/431 |
| 5,527,933 A | * | 6/1996 | Boutevin et al. | 556/421 |
| 6,087,521 A | * | 7/2000 | Jung et al. | 556/435 |
| 6,278,011 B1 | * | 8/2001 | Chen et al. | 556/431 |

FOREIGN PATENT DOCUMENTS

JP    A3197484    8/1991

OTHER PUBLICATIONS

CRC Handbook of Chemistry and Physics, 1984, p. C–515.*

* cited by examiner

Primary Examiner—Margaret G. Moore
(74) Attorney, Agent, or Firm—Birch, Stewart, Kolasch & Birch, LLP (57) ABSTRACT

A novel organosilicon compound obtained by introducing an alkylene group or analogue instead of the oxygen atom in an Si—O—Si linkage is capable of hydrosilylation reaction with another compound having a vinyl group to form a hydrosilylated derivative which is less prone to decomposition under acidic or basic conditions.

3 Claims, 4 Drawing Sheets

ORGANOSILICON COMPOUNDS

This invention relates to novel organosilicon compounds which are useful as an addition reaction crosslinking agent.

BACKGROUND OF THE INVENTION

Rubber compositions of the addition reaction curing type generally contain base polymers having alkenyl groups such as vinyl groups, compounds having hydrogen atoms directly attached to silicon atoms (i.e., SiH groups), and addition reaction catalysts such as platinum group catalysts. Curing takes place through the mechanism that the SiH groups add to alkenyl groups on the base polymer.

Many organosilicon compounds having SiH groups are known. One typical compound described in JP-A 3-197484 has the structure in which a SiH group is bonded through an oxygen atom to a silicon atom having a fluoroalkyl substituent as shown below.

This compound is capable of hydrosilylation reaction with another compound having a vinyl group and useful as a starting material from which various derivatives are synthesized. Using this compound, for instance, modifiers, resin or rubber crosslinking agents, surfactants and additives can be synthesized.

However, since this compound has an Si—O—Si linkage of the siloxane type in its molecule, this compound suffers from the likelihood of cleavage of the siloxane bond under such rigorous conditions as exposure to elevated temperature in the presence of acids or basic materials.

SUMMARY OF THE INVENTION

An object of the invention is to provide a novel SiH group-bearing organosilicon compound capable of hydrosilylation reaction with another compound having a vinyl group to form a hydrosilylated derivative which is less prone to decomposition under acidic or basic conditions.

The inventors have found that an organosilicon compound obtained by introducing an alkylene group or analogue instead of the oxygen atom in an Si—O—Si linkage is capable of hydrosilylation reaction with another compound having a vinyl group to form a hydrosilylated derivative which is less prone to decomposition under acidic or basic conditions.

The invention provides an organosilicon compound of the following general formula (1).

Herein "a" and "b" each are 0 or 1, "a" and "b" are not 0 at the same time. Z is hydrogen, —R, —M or —Q—Rf when either one of "a" and "b" is 0, and Z is —Q—, —Rf'— or —Q—Rf'—Q— when both "a" and "b" are 1. R is a monovalent hydrocarbon group of 1 to 6 carbon atoms and may be the same or different. M is a group of the following formula (2):

wherein m is an integer of 1 to 4 and R is as defined above. Q is a divalent hydrocarbon group of 1 to 15 carbon atoms which may contain an ether bond. Rf is a monovalent perfluoroalkyl or perfluorooxyalkyl group. Rf' is a divalent perfluoroalkylene or perfluorooxyalkylene group. The letter s is 1, 2 or 3, and t is 0, 1, 2 or 3.

DESCRIPTION OF THE PREFERRED EMBODIMENT

Formula (1) is described in detail. Letters "a" and "b" each are 0 or 1, excluding a=b=0. When either one of "a" and "b" is 0, Z is a monovalent group, specifically hydrogen, —R, —M or —Q—Rf. When both "a" and "b" are 1, Z is a divalent group, specifically —Q—, —Rf'— or —Q—Rf'—Q—.

R, which may be the same or different, stands for monovalent hydrocarbon groups of 1 to 6 carbon atoms, for example, alkyl groups such as methyl, ethyl, propyl, isopropyl, butyl, isobutyl, tert-butyl, pentyl, neopentyl and hexyl, alkenyl groups such as vinyl and allyl, and phenyl. Methyl and phenyl are preferred among others.

M is a group of the formula (2) wherein m is an integer of 1 to 4 and R is as defined above.

Q stands for divalent hydrocarbon groups of 1 to 15 carbon atoms, preferably 1 to 12 carbon atoms, more preferably 1 to 10 carbon atoms, which may contain an ether bond (—O—). Examples include alkylene groups such as methylene, ethylene, propylene, methylethylene, butylene and hexamethylene, cycloalkylene groups such as cyclohexylene, arylene groups such as phenylene, tolylene, xylylene, naphthylene and biphenylene, and combinations of any. Also exemplary of Q are divalent groups having an oxygen atom in their backbone structure. Herein the oxygen atom intervenes in the form of —O—.

Rf is a monovalent perfluoroalkyl or perfluorooxyalkyl group, and Rf' is a divalent perfluoroalkylene or perfluorooxyalkylene group. The preferred monovalent perfluoroalkyl groups are those of the formula:

wherein g is an integer of 1 to 20, preferably 2 to 10. The preferred divalent perfluoroalkylene groups are those of the formula:

wherein g is an integer of 1 to 20, preferably 2 to 10.

The preferred monovalent perfluorooxyalkyl groups are those of 1 to 500 carbon atoms, more preferably 1 to 300 carbon atoms, even more preferably 1 to 200 carbon atoms. Suitable examples are given below.

Letter h is an integer of 1 to 5.

The preferred divalent perfluorooxyalkylene groups are those of 1 to 500 carbon atoms, more preferably 1 to 300 carbon atoms, even more preferably 1 to 200 carbon atoms. Suitable examples are given below.

The sum of i+j is an integer of 2 to 100.

$$-(CF_2O)_e-(CF_2CF_2O)_f-CF_2-$$

Letters e and f each are an integer of 1 to 50.

Preferred examples of the organosilicon compound are those of the following general formulas (3) and (4).

Herein R' is a lower alkyl or phenyl group, k is an integer of 1 to 8, and p and q each are 1, 2 or 3.

Herein R, Rf and Q are as defined above, n is an integer of 1 to 4, and x is an integer of 1 to 3.

Illustrative examples of the organosilicon compound are given below. These examples are typical, although the invention is not limited thereto. Herein, Me is methyl and Ph is phenyl.

m = 1–4, n = 1–8 m = 1–4, n = 1–8

The organosilicon compound of formula (1) wherein a=b=1 can be synthesized by adding a monochlorosilane of the following general formula (6) to a polyfunctional vinyl compound of the following general formula (5), followed by reduction.

(5)

(6)

Herein, R, Z, s and t are as defined above.

Particularly when it is desired to produce the compound of formula (3), a polyfunctional vinyl compound of the following general formula (5a) and a monochlorosilane of the following general formula (6a) are useful.

(5a)

(6a)

Herein, R', k, p and q are as defined above.

Where a polyfunctional vinyl compound of formula (5a) wherein p=q=3 is used, for example, reaction proceeds according to the following scheme.

$\downarrow$ Pt compound $\downarrow$ reducing agent

The addition reaction using the platinum compound can be conducted by a conventional technique under well-known conditions. In the subsequent reducing reaction, LiAlH$_4$ and the like may be used as the reducing agent. The reducing reaction can be conducted by a conventional technique under well-known conditions.

In preparing the organosilicon compound of formula (1) wherein either one of "a" and "b" is 0, specifically a=1 and b=0, a compound of the following general formula (7) is used, for example.

(7)

$$Z-\underset{\underset{R_{3-s}}{|}}{SiCl_2}$$

Herein, R, Z and s are as defined above.

Particularly when it is desired to produce the compound of formula (4), synthesis can be effected according to the following scheme using a compound of the following general formula (7a).

The organosilicon compound of formula (4) wherein n=1 can be produced by preparing a Grignard reagent of chloromethyldimethylsilane and reacting it with a chlorosilane of formula (7a). Preparation of the Grignard reagent is effected by reacting magnesium with chloromethyldimethylsilane in tetrahydrofuran (THF). The Grignard reagent is then reacted with the chlorosilane, with the preferred amount of chlorosilane being 0.70 to 0.95 equivalent per equivalent of the Grignard reagent.

Preferred examples of the chlorosilane of formula (7a) used herein are those of the following structural formulas.

The reaction of the chlorosilane of formula (7a) with the Grignard reagent of chloromethyldimethylsilane may be effected at about 30 to 70° C. for about 1 to 20 hours. Following the reaction, the reaction mixture is admitted into dilute hydrochloric acid, in which the magnesium salt is dissolved, and an organic phase containing the end product is separated from an aqueous phase. An excess amount of hydrochloric acid is preferably used so that the aqueous phase is maintained acidic. By distilling the thus separated organic phase, the organosilicon compound of formula (4) can be isolated.

The organosilicon compound of formula (4) wherein n=2 can be produced by reacting a corresponding chlorosilane of formula (7a) with a vinyl Grignard reagent such as $CH_2$=CHMgCl or $CH_2$=CHMgBr to introduce a vinyl group, and adding chlorodimethylsilane to the product, followed by reduction.

The reaction of the chlorosilane of formula (7a) with the vinyl Grignard reagent may be effected by adding the chlorosilane to the THF solution of the vinyl Grignard reagent as prepared. Preferably the chlorosilane of formula (7a) is used in an amount of 0.80 to 0.95 equivalent per equivalent of the Grignard reagent. The above-exemplified chlorosilanes may be used as well. The reaction of the chlorosilane of formula (7a) with the vinyl Grignard reagent may be effected at about 30 to 70° C. for about 10 minutes to about 2 hours. Following the reaction, the reaction mixture is admitted into dilute hydrochloric acid, in which the magnesium salt is dissolved, and an organic phase containing the end product is separated from an aqueous phase. By distilling the thus separated organic phase, the intermediate (a) having a vinyl group introduced therein is obtained.

Chlorodimethylsilane is then added to the intermediate (a) to form an intermediate (b). This reaction can be effected by adding chlorodimethylsilane to a mixture of the intermediate (a) and a chloroplatinic acid catalyst. The reaction may be effected at about 50 to 80° C. for about 10 minutes to about 2 hours.

A solvent may be used in the above reaction. Suitable solvents include hexane, toluene, xylene, butyl ether, THF, and bistrifluoromethylbenzene.

By reducing the intermediate (b), an end organosilicon compound is obtained. The preferred reducing agent is $LiAlH_4$. This reaction is effected by adding the intermediate (b) dropwise to a THF solution of $LiAlH_4$. The rate of addition is desirably adjusted such that the reaction mixture remains at a temperature of 20 to 50° C. Following the dropwise addition, the reaction mixture is admitted into dilute hydrochloric acid, from which an organic phase containing the end compound is separated. Distillation yields the end organosilicon compound of the invention.

The organosilicon compounds of the invention are useful in a variety of applications as crosslinking agents, modifying intermediates, etc.

EXAMPLE

Examples of the invention are given below by way of illustration and not by way of limitation.

Example 1

A 1000-ml four-necked flask equipped with a stirrer, thermometer, Dimroth condenser and dropping funnel was charged with 98.4 g (0.4 mol) of bis(trivinylsilyl)ethane and 1.0 g of a toluene solution containing a diivinyltetramethyldisiloxane complex of chloroplatinic acid (Pt concentration 0.5 wt %). With stirring, the solution was heated to 90° C. From the dropping funnel, 249.5 g (2.64 mol) of dimethylchlorosilane was added dropwise at 90 to 100° C. over 2 hours. The reaction mixture was ripened at 90 to 100° C. for 3 hours. It was cooled and distilled in vacuum, collecting 286 g of a fraction having a boiling point of 240 to 250° C. under $2.5 \times 10^{-4}$ Torr. On $^1$H-NMR analysis, the fraction was identified to be the following compound.

$^1$H-NMR analysis (TMS standard, ppm)

δ 0.05 (≡Si—CH$_3$; 18H)

δ 0.35 (≡Si—CH$_2$—; 14H)

Next, a 1000-ml four-necked flask equipped with a stirrer, thermometer, Dimroth condenser and dropping funnel was charged with 150 g of toluene and 30.1 g (0.79 mol) of LiAlH$_4$. With stirring, 300 g of THF was added dropwise from the dropping funnel, following which a mixture of 286 g (0.35 mol) the above-collected fraction and 500 g toluene was added dropwise from the dropping funnel. The reaction mixture was ripened below 30° C. for 2 hours, following which 80 g of ethyl acetate was added dropwise from the dropping funnel. The reaction mixture was then admitted into 3 liters of 1N hydrochloric acid, which was washed with water. Only the upper layer was taken out by separation, dried over sodium sulfate and filtered. The filtrate was distilled in vacuum, collecting 187.3 g (yield 87.8%) of a fraction having a boiling point of 186 to 189° C. under $2.5 \times 10^{-4}$ Torr. The fraction was analyzed by $^1$H-NMR and infrared absorption spectroscopy, with the results shown below.

$^1$H-NMR analysis (TMS standard, ppm)

δ 0.05 (≡Si—CH$_3$; 18H)

δ 0.35 (≡Si—CH$_2$—; 14H)

δ 3.70 (≡Si—H; 3H)

Figure 1:
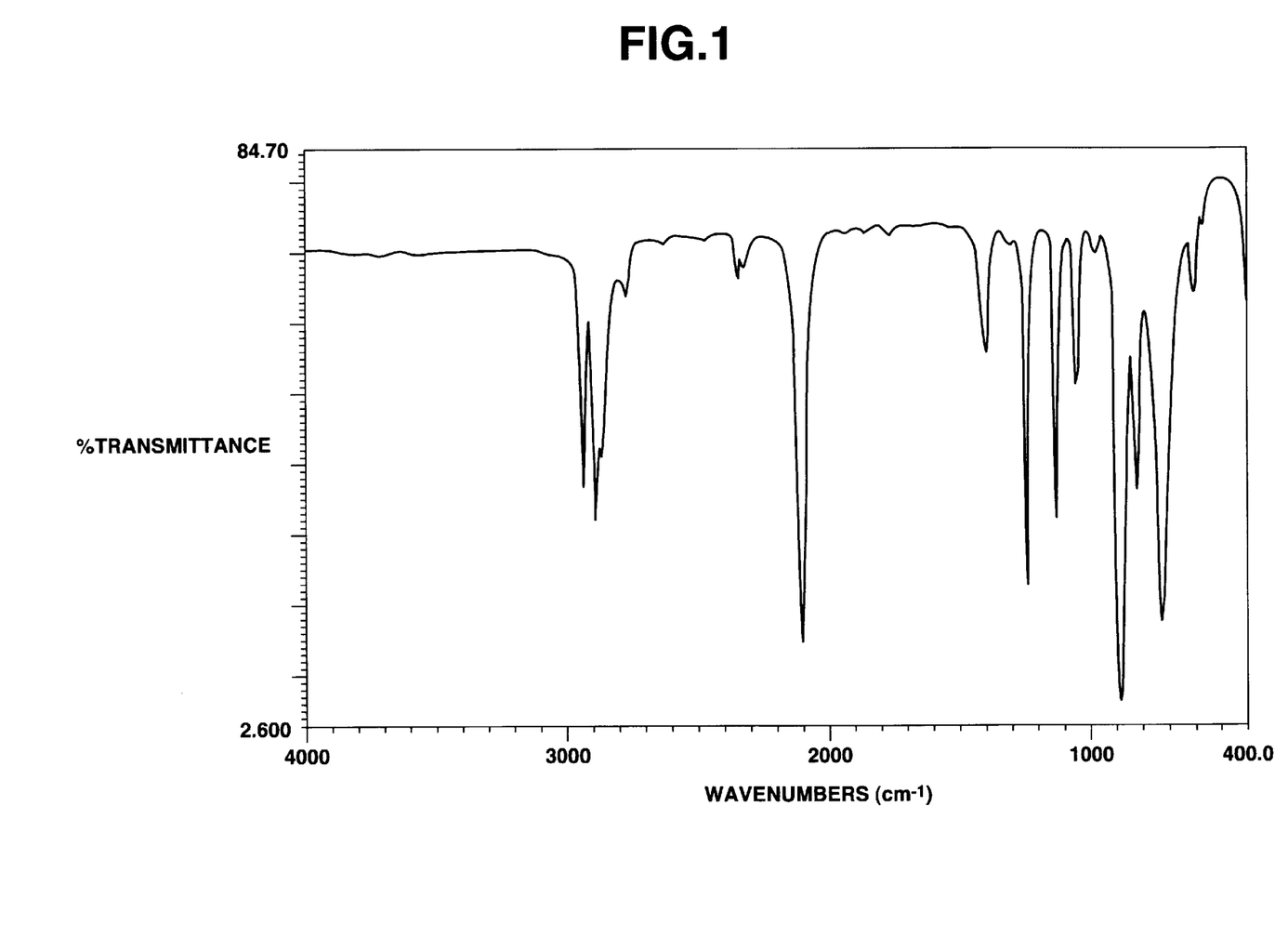
FIG. 1 is the IR spectrum of the compound produced in Example 1.

IR spectrum (FIG. 1)

2,109 cm$^{-1}$ υ Si—H

The functional group equivalent of the compound was quantitated, finding $9.94 \times 10^{-3}$ mol/g. Accordingly, the compound was identified to be an organosilicon compound of the following structural formula.

Example 2

With stirring, 9.3 g of magnesium powder, 120 ml of THF and an aliquot of iodine were heated until the THF refluxed. When the brown color of iodine vanished away, 40.0 g of chloromethyldimethylsilane was slowly added dropwise. The rate of addition was adjusted such that the reaction mixture was kept at a temperature of 50 to 60° C. Following the dropwise addition, stirring was continued at 60° C. for 1 hour. Then 50.8 g of n-C$_8$F$_{17}$CH$_2$CH$_2$SiCl$_3$ was added dropwise over 20 minutes. Following the dropwise addition, stirring was continued at 65° C. for about 15 hours. The reaction mixture was admitted into a 2N hydrochloric acid aqueous solution. The organic phase was taken out, washed with water and distilled. A product of the following formula was obtained.

Boiling point: 140° C. under 1 mmHg

Amount: 43.9 g

Yield: 72%

Figure 2:
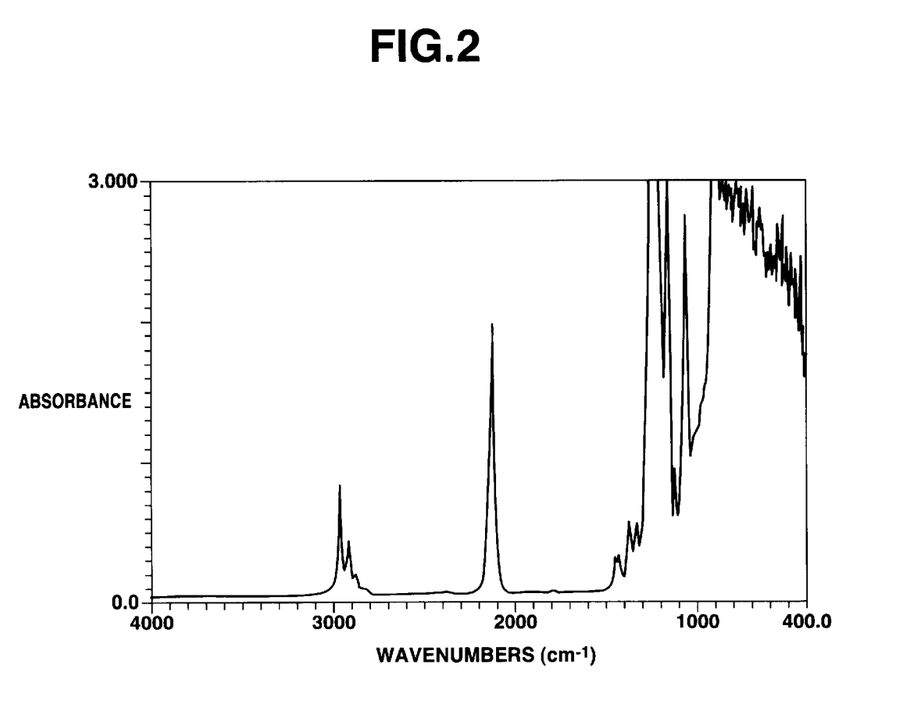
FIG. 2 is the IR spectrum of the compound produced in Example 2.

The IR spectrum of this product is shown in FIG. 2.

Example 3

A THF solution containing 2 mol of CH$_2$=CHMgBr was prepared. Then 349 g of n-C$_8$F$_{17}$CH$_2$CH$_2$SiCl$_3$ was added dropwise to the THF solution at 30 to 50° C. Following the dropwise addition, stirring was continued for about 2 hours. The reaction mixture was admitted into a 1N hydrochloric acid aqueous solution. The organic phase was taken out, washed with water and distilled, obtaining an intermediate (1) of the following structure.

Boiling point: 130° C. under 20 mmHg

Amount: 270 g

Yield: 81%

Intermediate (1)

A mixture of 250 g of the intermediate (1), 150 g of toluene and 0.2 g of a butanol solution of chloroplatinic acid (Pt concentration 2 wt %) was heated at 70° C. With stirring, 140 g of chlorodimethylsilane was added dropwise to the mixture. The rate of addition was adjusted such that the reaction mixture was kept at a temperature of 70 to 100° C. Following the dropwise addition, the reaction mixture was allowed to stand for about 1 hour. The reaction mixture was distilled, obtaining an intermediate (2) of the following structure.

Boiling point: 193° C. under 1 mmHg

Amount: 362 g

Yield: 96%

Intermediate (2)

After 13.6 g of LiAlH$_4$ was dissolved in 250 g of THF, a mixture of 250 g of the intermediate (2) and 250 g of toluene was added dropwise to the solution. The reactor was cooled and the rate of addition was adjusted such that the reaction mixture remained at a temperature of 20 to 30° C. during the dropwise addition. Following the dropwise addition, stirring was continued for about one hour. The reaction mixture was admitted into a 1N hydrochloric acid aqueous solution. The organic phase was separated, washed with water and distilled, obtaining a product of the following structure.

Figure 3:
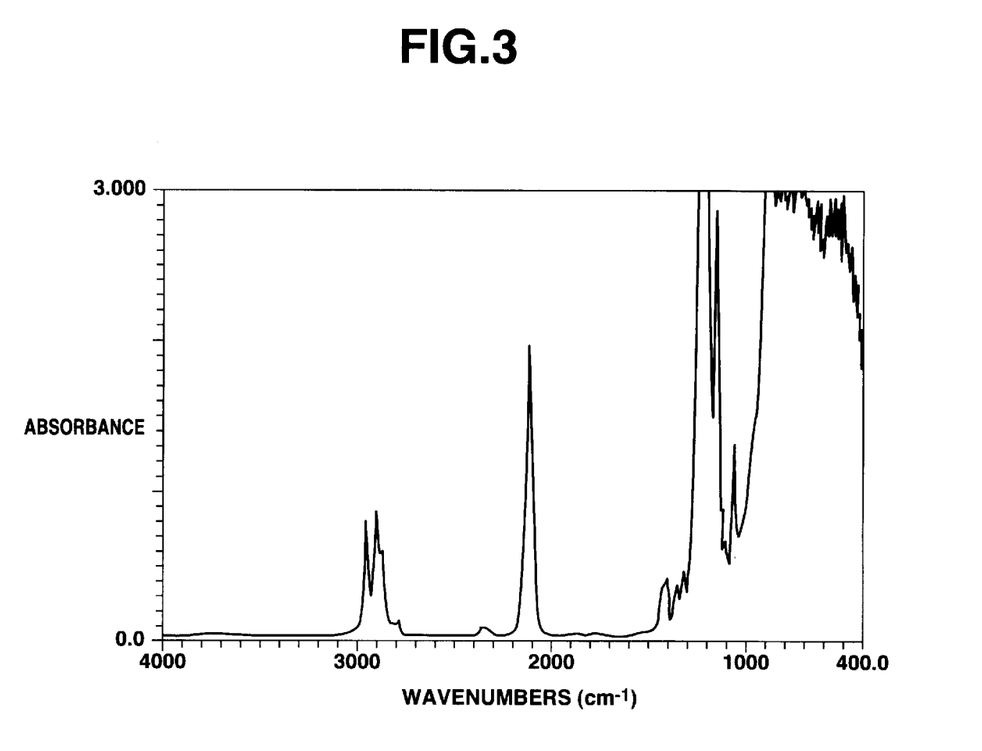
FIG. 3 is the IR spectrum of the compound produced in Example 3.

Boiling point: 162° C. under 1 mmHg
Amount: 114 g
Yield: 52%
The IR spectrum of this product is shown in FIG. 3.

Example 4

With stirring, 16.5 g of magnesium powder, 200 ml of THF and an aliquot of iodine were heated until the THF refluxed. When the brown color of iodine vanished away, 70.0 g of chloromethyldimethylsilane was slowly added dropwise. The rate of addition was adjusted such that the reaction mixture was kept at a temperature of 50 to 60° C. Following the dropwise addition, stirring was continued at 60° C. for one hour. Then a mixture of 22.3 g of $Cl_3SiCH_2CH_2SiCl_3$ and 22.3 g of toluene was added dropwise at 50 to 60° C. over 20 minutes. Following the dropwise addition, the reaction mixture was stirred at 62° C. for about 24 hours. The reaction mixture was admitted into 500 ml of a 2N hydrochloric acid aqueous solution. The organic phase was further washed with 500 ml of a 1N hydrochloric acid aqueous solution. There was recovered 63 g of an organic phase containing the reaction product. On GC-MS analysis, the solution was found to contain 23% of a product of the following structure. $M^+=522$.

Example 5

With stirring, 20.8 g of magnesium powder, 300 ml of THF and an aliquot of iodine were heated until the THF refluxed. When the brown color of iodine vanished away, 89.2 g of chloromethyldimethylsilane was slowly added dropwise. The rate of addition was adjusted such that the reaction mixture was kept at a temperature of 50 to 60° C. Following the dropwise addition, stirring was continued at 60° C. for one hour. Then a mixture of 100.0 g of a compound of the following structure:

and 65 g of toluence was added dropwise at 28 to 60° C. over 30 minutes. Following the dropwise addition, the reaction mixture was stirred at 65° C. for about 2 hours. The reaction mixture was admitted into a 2N hydrochloric acid aqueous solution. The organic phase was recovered, washed with water, and distilled off to obtain a product of the following structure.

Boiling point: 205–217° C./1 mmHg
Amount: 94.4 g
Yield: 75%

Figure 4:
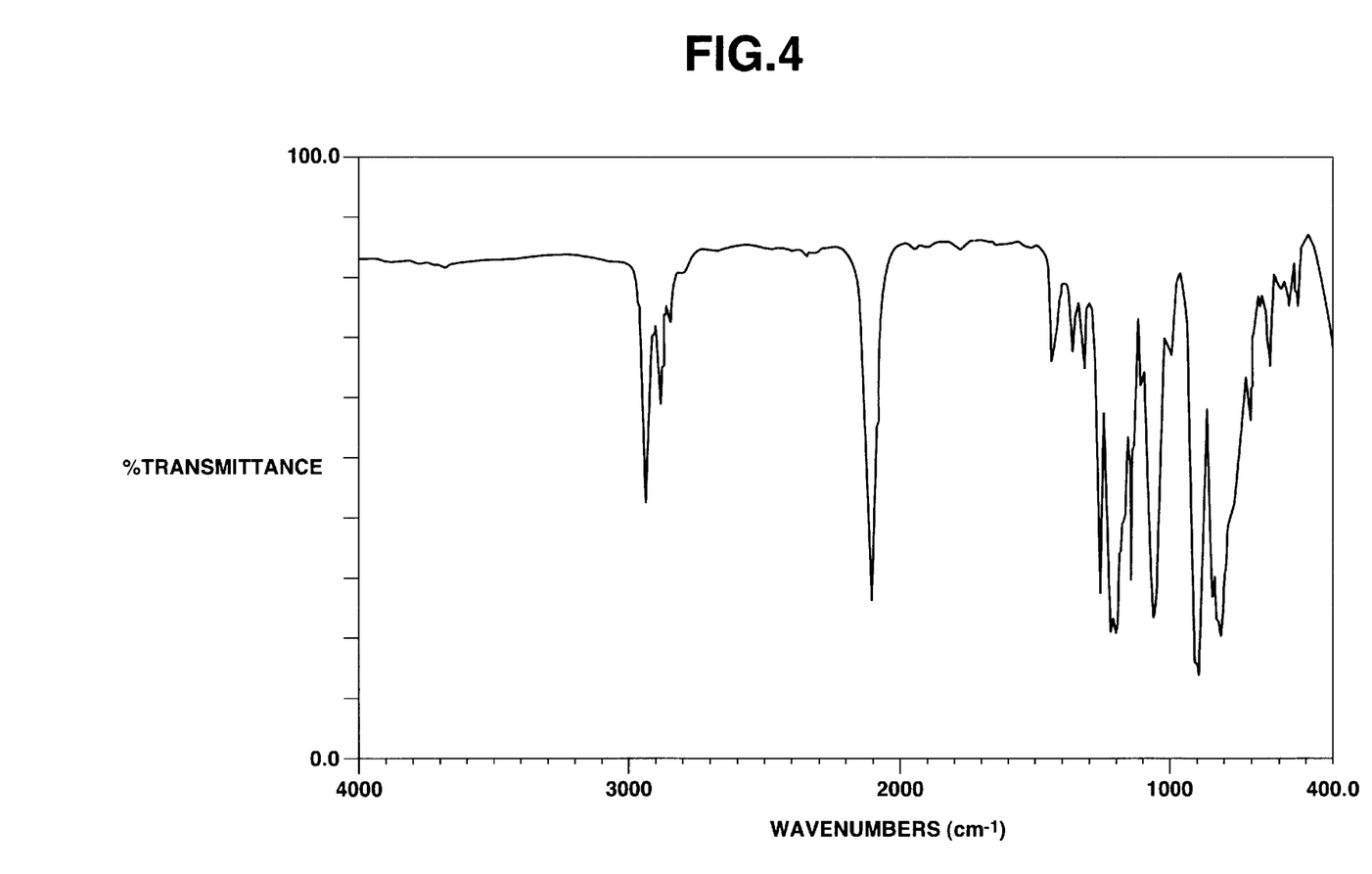
FIG. 4 is the IR spectrum of the compound produced in Example 5.

The IR spectrum of this product is shown in FIG. 4.

There have been described organosilicon compounds which are capable of hydrosilylation reaction with other compounds having a vinyl group and thus useful as intermediates. Since the inventive compounds are free of an Si—O—Si linkage of the siloxane type, hydrosilylated derivatives thereof are not readily decomposable under acidic or basic conditions.

Japanese Patent Application No. 2000-124108 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organosilicon compound of the following general formula (1):

wherein "a" and "b" each are 0 or 1, "a" and "b" are not 0 at the same time, Z is —R, —M or —Q—Rf, and s and t are 1, 2, or 3, respectively, when either one of "a" and "b" is 0, Z is —Q—, —Rf'— or —Q—Rf'—Q— and s is 1, 2, or 3 and t is 0, 1, 2, or 3, when both "a" and "b" are 1, R is a monovalent hydrocarbon group of 1 to 6 carbon atoms and may be the same or different, M is a group of the following formula (2)

wherein m is an integer of 1 to 4 and R is as defined above,

Q is a divalent hydrocarbon group of 1 to 15 carbon atoms which may contain an ether bond, Rf is a monovalent perfluoroalkyl or perfluorooxyalkyl group, and Rf' is a divalent perfluoroalkylene or perfluorooxyalkylene group.

2. The organosilicon compound of claim 1 having the following general formula (3):

wherein R' is a lower alkyl or phenyl group, k is an integer of 1 to 8, and p and q each are 1, 2 or 3.

3. The organosilicon compound of claim 1 having the following general formula (4):

wherein R, Rf and Q are as defined above, n is an integer of 1 to 4, and x is an integer of 1 to 3.

* * * * *